(12) United States Patent
Bakken et al.

(10) Patent No.: US 7,133,718 B2
(45) Date of Patent: Nov. 7, 2006

(54) METHOD AND APPARATUS FOR TEMPORARILY VARYING A PARAMETER IN AN IMPLANTABLE MEDICAL DEVICE

(75) Inventors: Earl E. Bakken, North Kona Coast, HI (US); Rebecca M. Bergman, North Oaks, MN (US); William J. Combs, Minnetonka, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 589 days.

(21) Appl. No.: 10/465,351

(22) Filed: Jun. 19, 2003

(65) Prior Publication Data

US 2004/0260348 A1    Dec. 23, 2004

(51) Int. Cl.
*A61N 1/362* (2006.01)
(52) U.S. Cl. .......................................................... 607/9
(58) Field of Classification Search ...................... None
See application file for complete search history.

(56) References Cited

U.S. PATENT DOCUMENTS

| | | |
|---|---|---|
| 3,593,718 A | 7/1971 | Krasner et al. |
| 3,921,642 A | 11/1975 | Preston et al. |
| 3,941,135 A | 3/1976 | Sturm et al. |
| 4,374,382 A | 2/1983 | Markowitz |
| 4,428,378 A | 1/1984 | Anderson et al. |
| 4,702,253 A | 10/1987 | Nappholz et al. |
| 4,711,245 A | 12/1987 | Higgins et al. |
| 4,776,338 A | 10/1988 | Lekholm et al. |
| 4,795,542 A | 1/1989 | Ross et al. |
| 5,088,488 A | 2/1992 | Markowitz et al. |
| 5,107,833 A | 4/1992 | Barsness |
| 5,117,824 A | 6/1992 | Keimel et al. |
| 5,168,871 A | 12/1992 | Grevious |
| 5,292,343 A | 3/1994 | Blanchette et al. |

(Continued)

FOREIGN PATENT DOCUMENTS

EP     089014 B1    10/1983

(Continued)

OTHER PUBLICATIONS

Viitasalo, et al., "Ventricular Arrhythmias During Exercise Testing, Jogging, and Sedentary Life: A Compative Study of Healthy Physically Active Men, Healthy Sedentary Men, and Men with Previous Myocardial Infarction", *Chest*, vol. 76, pp. 21-26, Jul. 1979.

(Continued)

*Primary Examiner*—Robert E. Pezzuto
*Assistant Examiner*—Kristen Mullen
(74) *Attorney, Agent, or Firm*—Michael C. Soldner; Girma Wolde-Michael

(57) ABSTRACT

A method and apparatus for varying a parameter in an implantable medical device that includes a plurality of electrodes stimulating heart tissue and sensing cardiac signals, a timing and control device controlling the stimulation of heart tissue by the plurality of electrodes and measuring intervals between the sensed cardiac signals, a storage device storing the measured intervals, and a microprocessor. The microprocessor determines heart rate variability in response to the stored intervals, compares the determined heart rate variability to a predetermined target rate profile, adjusts the parameter from a first setting to a second setting different from the first setting in response to the comparing of the determined heart rate variability and the predetermined target rate profile, and adjusts the parameter from the second setting to a termination setting in response to a termination event or expiration of a first predetermined time period.

44 Claims, 13 Drawing Sheets

U.S. PATENT DOCUMENTS

| | | | |
|---|---|---|---|
| 5,304,208 A | 4/1994 | Inguaggiato et al. | |
| 5,312,452 A * | 5/1994 | Salo | 607/17 |
| 5,314,450 A | 5/1994 | Thompson | |
| 5,324,315 A | 6/1994 | Grevious | |
| 5,342,404 A | 8/1994 | Alt et al. | |
| 5,354,319 A | 10/1994 | Wyborny et al. | |
| 5,383,909 A | 1/1995 | Keimel | |
| 5,464,434 A | 11/1995 | Alt | |
| 5,466,245 A * | 11/1995 | Spinelli et al. | 607/17 |
| 5,476,483 A | 12/1995 | Bornzin et al. | |
| 5,545,186 A | 8/1996 | Olson et al. | |
| 5,562,711 A | 10/1996 | Yerich et al. | |
| 5,622,428 A | 4/1997 | Bonnet | |
| 5,733,312 A | 3/1998 | Schloss et al. | |
| 5,755,736 A | 5/1998 | Gillberg et al. | |
| 5,766,288 A | 6/1998 | Thiele et al. | |
| 5,814,087 A | 9/1998 | Renirie | |
| 5,836,975 A | 11/1998 | DeGroot | |
| 5,891,044 A | 4/1999 | Golosarky et al. | 600/509 |
| 5,891,176 A | 4/1999 | Bornzin | |
| 5,919,209 A * | 7/1999 | Schouten | 607/2 |
| 5,957,957 A | 9/1999 | Sheldon | |
| 5,964,788 A | 10/1999 | Greenhut | |
| 5,991,661 A | 11/1999 | Park et al. | |
| 6,049,735 A | 4/2000 | Hartley et al. | |
| 6,055,454 A | 4/2000 | Heemels | |
| 6,058,328 A | 5/2000 | Levine et al. | 607/14 |
| 6,122,536 A | 9/2000 | Sun et al. | |
| 6,128,534 A | 10/2000 | Park et al. | |
| 6,141,590 A | 10/2000 | Renirie et al. | |
| 6,249,700 B1 | 6/2001 | Alt | |
| 6,253,107 B1 | 6/2001 | Albrecht et al. | 607/9 |
| 6,529,772 B1 | 3/2003 | Carlson et al. | |
| 6,766,194 B1 * | 7/2004 | Kroll | 607/9 |
| 2002/0082664 A1 | 6/2002 | Kerver | |
| 2003/0074029 A1 | 4/2003 | Deno et al. | 607/23 |

OTHER PUBLICATIONS

Park, et al., "Activity-Controlled Circadian Base Rate", *PACE*, vol. 21, pp. 2182-2186, Nov. 1998, Part II.

"Intraoperative Transesophageal Dobutamine Stress Echocardiography for Perioperative Risk Assessment in Patients with an Increased Risk of Ischemic Cardiac Events", http://www.anaesthesie.ch/eng/tee/tee.htm.

Malik, et al., Heart Rate Variability: Standards of Measurement, Physiological Interpretation, and Clinical Use, *Circulation*, vol. 93(5), pp. 1043-1065, Mar. 1, 1996.

* cited by examiner

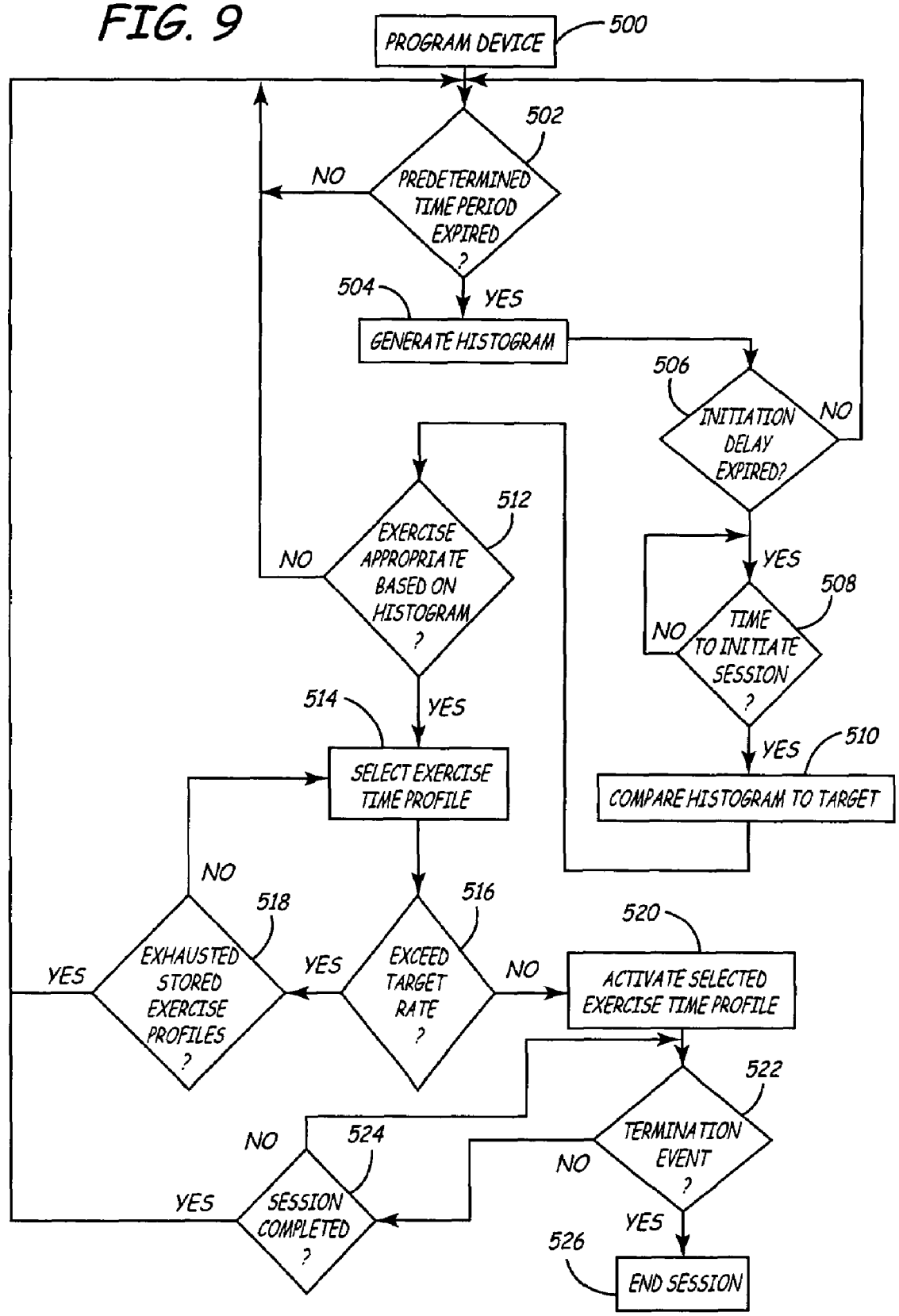

METHOD AND APPARATUS FOR TEMPORARILY VARYING A PARAMETER IN AN IMPLANTABLE MEDICAL DEVICE

FIELD OF THE INVENTION

The present invention relates generally to implantable medical devices, and in particular, the present invention relates to an implantable medical device that provides variations of a baseline heart rate to reflect activities of daily living and circadian variation in patients who are sedentary to improve the strength and functioning of the heart.

BACKGROUND OF THE INVENTION

Several advances in pacing have occurred over the years by providing improved methods in sensing natural pacing rhythms. For instance, in demand pacing devices, the objective is to provide stimulatory pulses in the absence of the natural heartbeat. That is, the pacemaker or pacemaker/cardioverter/defibrillator is designed to deliver a pulse at a fixed rate as long as no natural heartbeat is sensed. Sensing of the natural frequency of heartbeats can be done to accommodate changes in the natural pacing frequency such as during natural rhythms of sleep or exercise.

Benefits have recently been identified that tend to promote introducing a circadian variation to the rate-adaptive pacemaker base rate, i.e., lowering the base heart rate during sleep or during prolonged periods of inactivity. Several pacemakers or pacemaker/cardioverter/defibrillator are currently available that have two basal rates to more closely match diurnal or circadian heart rate variations (by programming two resting rates). U.S. Pat. No. 3,921,642 to Preston et al. discusses the advantages of providing a pacemaker capable of searching for and detecting the occurrence of natural resting basal heart rates within a predetermined range. U.S. Pat. No. 3,593,718 and in European Patent Application No. 0 089 014 describe pacemakers that respond to changes in respiration rate, for instance during exercise. Alternate means for sensing physical activity and adjusting the pacemaker rate accordingly are described in U.S. Pat. No. 4,776,338.

Clinical evidence is available that tends to show that patients with decreased heart rate variability die earlier than those with normal variability and are a predictor of arrhythmic cardiac death, myocardial infarction, rapid progression of atherosclerosis and death from heart failure. A possible correlation has been identified between sedentary lifestyle and risk of ventricular arrhythmias based on a comparison of occurrences of ventricular arrhythmias in healthy active vs. sedentary men, and men with previous myocardial infarction. Accordingly, the greatest number and highest grades of ventricular arrhythmias during exercise were found in healthy sedentary men.

It is also well know that naturally the heart goes through varied basal rates. For instance, during normal sleep patterns, the heart rate changes depending on the sleep state (e.g., REM sleep, etc.). That is, normally the heart rate is not fixed at a particular rate during sleep.

There is a growing population of patients having implantable pacemaker or pacemaker/cardioverter/defibrillator devices who are largely sedentary and who are therefore likely to be paced at their basal rate for much of the day, since they are unable to achieve any measurable amount of exercise on their own. However, since current adaptive rate pacemakers or pacemaker/cardioverter/defibrillators are designed to find a range of natural rhythms occurring in the patient, whether to slow them during sleep, or to increase the rate during physical activity, with the goal of sensing and establishing a pacing rate within a controlled range of preexisting rates, currently available pacemakers or pacemaker/cardioverter/defibrillators do not address the benefit of having periods of elevated pacing designed into the pacemaker, particularly where no natural rhythm for the elevated pacing rate has been established.

SUMMARY OF THE INVENTION

The present invention is directed to a method and apparatus for varying a parameter in an implantable medical device that includes a plurality of electrodes stimulating heart tissue and sensing cardiac signals, a timing and control device controlling the stimulation of heart tissue by the plurality of electrodes and measuring intervals between the sensed cardiac signals, a storage device storing the measured intervals, and a microprocessor determining heart rate variability in response to the stored intervals, comparing the determined heart rate variability to a predetermined target rate profile, adjusting the parameter from a first setting to a second setting different from the first setting in response to the comparing of the determined heart rate variability and the predetermined target rate profile, and adjusting the parameter from the second setting to a termination setting in response to expiration of a first predetermined time period.

According to an embodiment of the present invention, an implantable medical device includes means for stimulating heart tissue and sensing cardiac signals, means for controlling timing of the stimulation of heart tissue and measuring intervals between the sensed cardiac signals, means for determining heart rate variability in response to the stored intervals, means for comparing the determined heart rate variability to a predetermined target rate profile, means for adjusting the parameter from a first setting to a second setting different from the first setting in response to the comparing of the determined heart rate variability and the predetermined target rate profile, and adjusting the parameter from the second setting to a termination setting in response to expiration of a first predetermined time period, and means for selecting a first exercise time profile from stored exercise time profiles in response to the comparison of the determined heart rate variability to the predetermined target rate profile. Each of the stored exercise time profiles include an acceleration portion including a second time period and a first shape corresponding to adjusting the parameter from the first setting to the second setting, a steady-state portion including a first value corresponding to the second setting and a second value corresponding to the first predetermined time period, and a deceleration portion including a third time period and a second shape corresponding to adjusting the parameter from the second setting to the termination setting. The adjusting means adjusts the parameter from the second setting to the termination setting, prior to the first predetermined time period, in response to detecting one of a programming session, a magnet, a cardiac arrhythmia, spontaneous rate greater than the second setting, and rate response greater than the second setting.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein:

FIG. 9 is a flowchart of a method for varying a pacing rate in an implantable medical device according to the present invention;

DETAILED DESCRIPTION OF THE INVENTION

Figure 1:
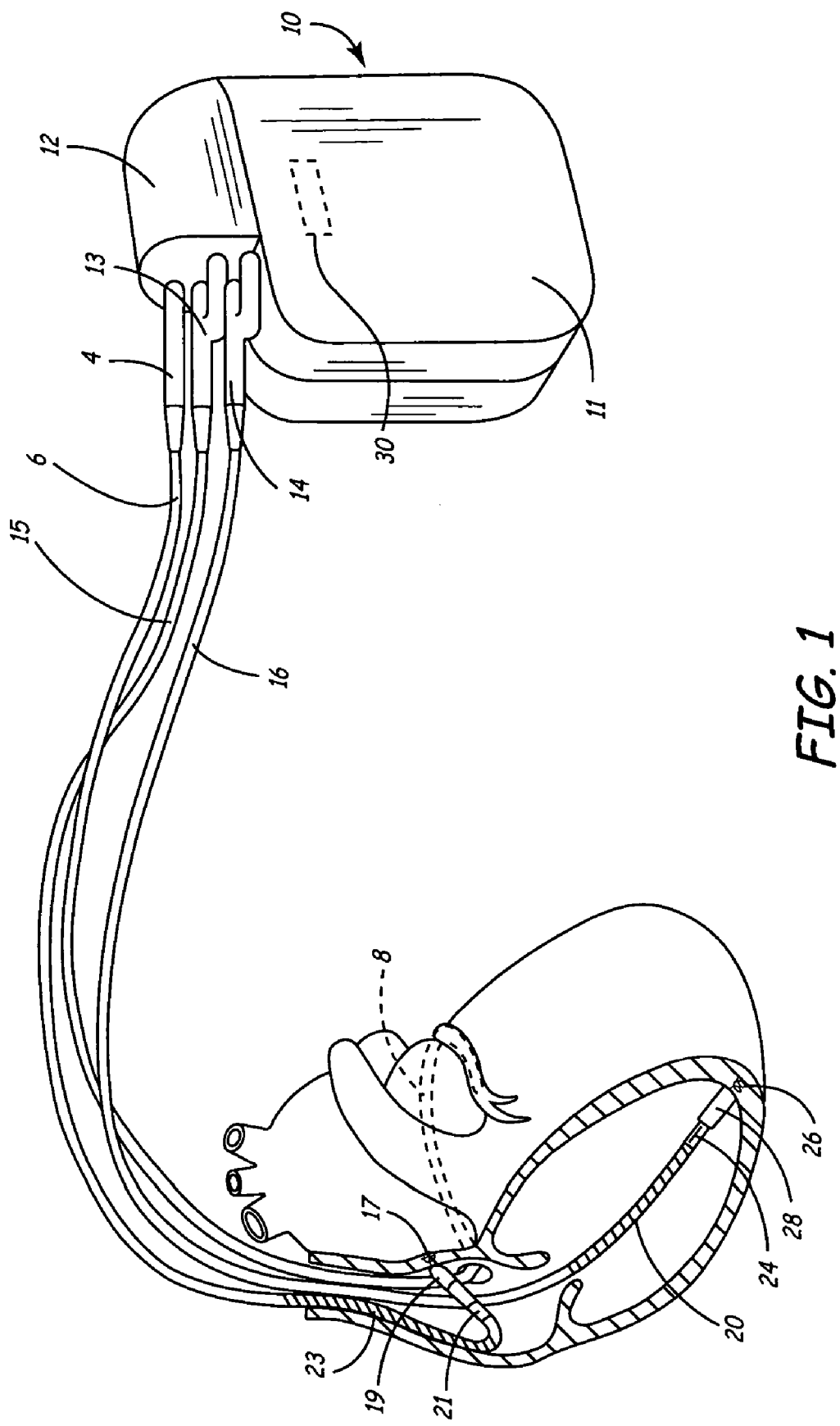
FIG. 1 is a schematic diagram of a pacemaker/cardioverter/defibrillator and lead set of a type in which the present invention may usefully be practiced.

FIG. 1 is a schematic diagram of a pacemaker/cardioverter/defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. At the proximal end of the lead is a bifurcated connector 14, which carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13, which carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor.

The pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors 4, 13 and 14 and interconnecting the leads to the circuitry within enclosure 11. A sensor 30 is illustrated schematically by broken outline, and may include one or more of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art. Sensor 30 may be used for regulation of pacing rate based upon demand for cardiac output and is utilized to provide variations of a baseline heart rate to reflect activities of daily living and circadian variation in patients who are sedentary and unable to exercise to improve the strength and functioning of the heart, as described below.

Optionally, insulation of the outward facing portion of the housing 11 of the pacemaker/cardioverter/defibrillator 10 may be provided or the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two lead system.

Figure 2:
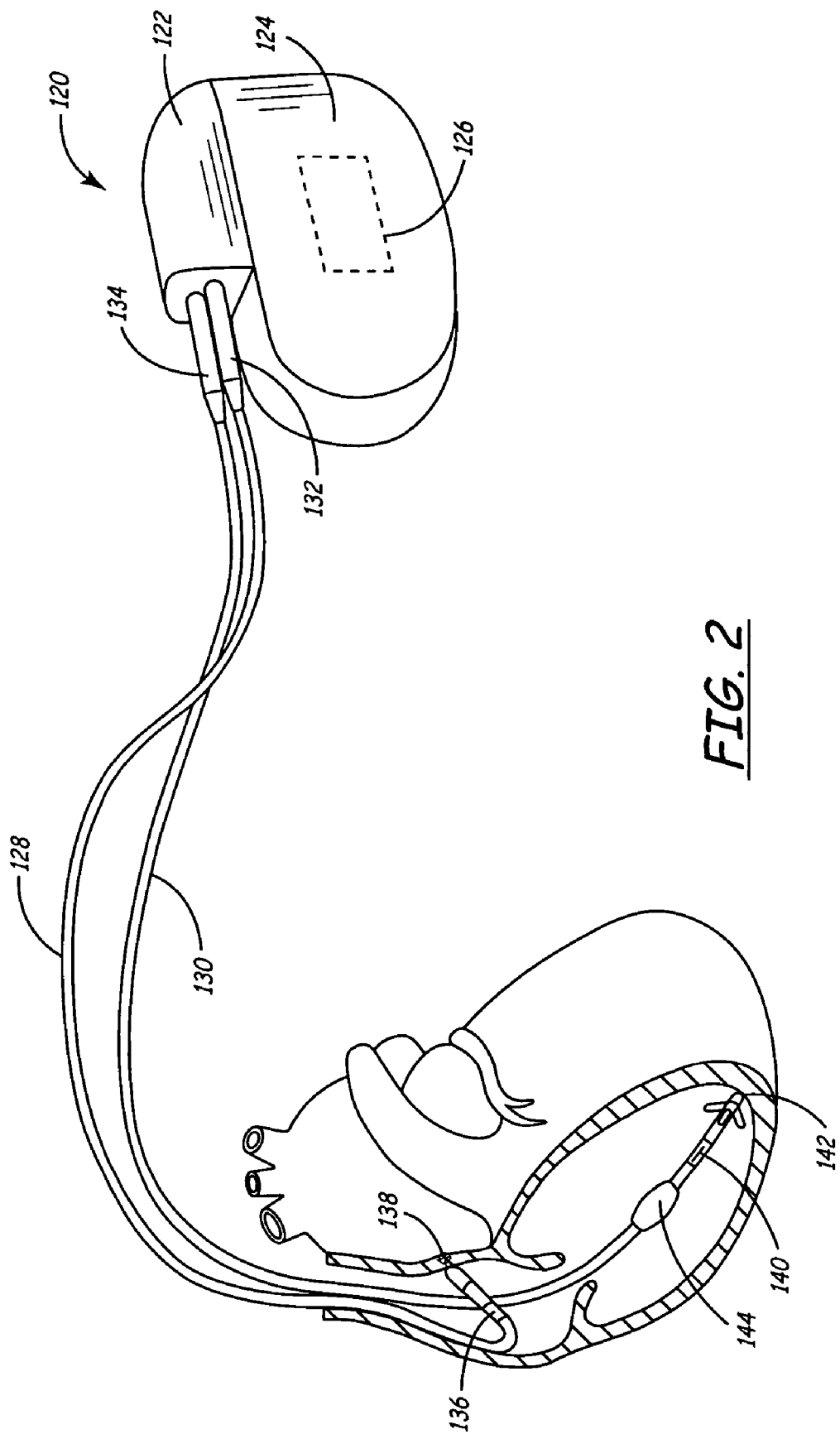
FIG. 2 is a schematic diagram of a cardiac pacemaker of a type appropriate for use in practicing the present invention in conjunction with its associated lead system, illustrated in relation to a patient's heart.

FIG. 2 is a schematic diagram of a cardiac pacemaker of a type appropriate for use in practicing the present invention in conjunction with its associated lead system, illustrated in relation to a patient's heart. The pacemaker 120 includes a hermetic enclosure 124 containing the electronic circuitry used for generating cardiac pacing pulses and for monitoring the patient's heart rhythm. An activity sensor 126 is illustrated schematically by broken outline, and may include one or more of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144, which may optionally be included in addition to or as an alternative to sensor 126, and which may take the form of an activity sensor, respiration sensor (potentially from impedance), accelerometer-based posture detector, heart rate detector, ischemia detector and other available physiological sensor known in the art for measuring heart hemodynamics and may be a piezoelectric transducer as known in the art as discussed above in conjunction with FIG. 1. One or both of sensors 126 and 144 can be utilized alone or in combination for rate responsive pacing and to provide variations of a baseline heart rate to reflect activities of daily living and circadian variation in patients who are sedentary and unable to exercise to improve the strength and functioning of the heart, as described below. Atrial lead 130 carries electrodes 136 and 138 and is employed for sensing and pacing the patient's atrium.

Figure 3:
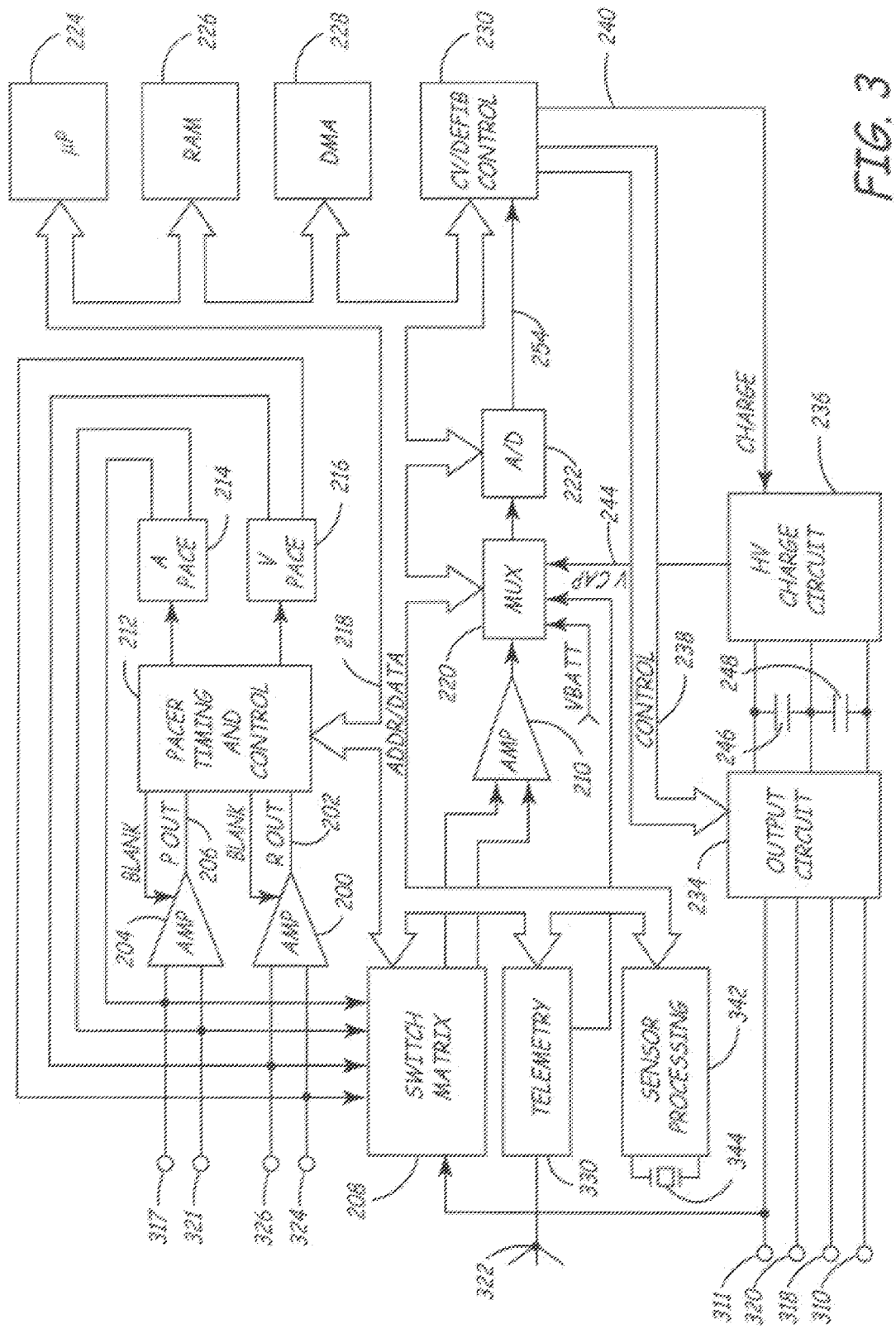
FIG. 3 is a functional schematic diagram of an implantable pacemaker/cardioverter/defibrillator of the type illustrated in FIG. 1, in which the present invention may usefully be practiced.

FIG. 3 is a functional schematic diagram of an implantable pacemaker/cardioverter/defibrillator of the type illustrated in FIG. 1, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to an electrode formed along the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety. However, any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

Telemetry circuit 330 receives downlink telemetry from and sends uplink telemetry to the patient activator by means of antenna 332. Data to be uplinked to the activator and control signals for the telemetry circuit are provided by microprocessor 224 via address/data bus 218. Received telemetry is provided to microprocessor 224 via multiplexer 220. The atrial and ventricular sense amp circuits 200, 204 produce atrial and ventricular EGM signals which also may be digitized and uplink telemetered to an associated programmer on receipt of a suitable interrogation command. The device may also be capable of generating so-called marker codes indicative of different cardiac events that it detects. A pacemaker with marker-channel capability is described, for example, in U.S. Pat. No. 4,374,382 to Markowitz, incorporated by reference herein in its entirety. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 3 includes an activity sensor 344, mounted to the interior surface of the device housing or to the hybrid circuit within the device housing and corresponds to sensor 30 of FIG. 1. The sensor 344 and sensor present in circuitry 342 may be employed in the conventional fashion described in U.S. Pat. No. 4,428,378 issued to Anderson et al, incorporated herein by reference in its entirety, to regulate the underlying pacing rate of the device in rate responsive pacing modes. In addition, sensor and circuitry 342 are utilized to provide variations of a baseline heart rate to reflect activities of daily living and circadian variation in patients who are sedentary and unable to exercise to improve the strength and functioning of the heart, as described below.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, PR intervals and R-P intervals, which measurements are stored in memory 226 and are used in conjunction with the present invention to measure heart rate variability and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al. or in U.S. Pat. No. 5,755,736 issued to Gillberg et al., both incorporated herein by reference in their entireties. However, any of the various arrhythmia detection methodologies known to the art might also usefully be employed in alternative embodiments of the invention.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

Figure 4:
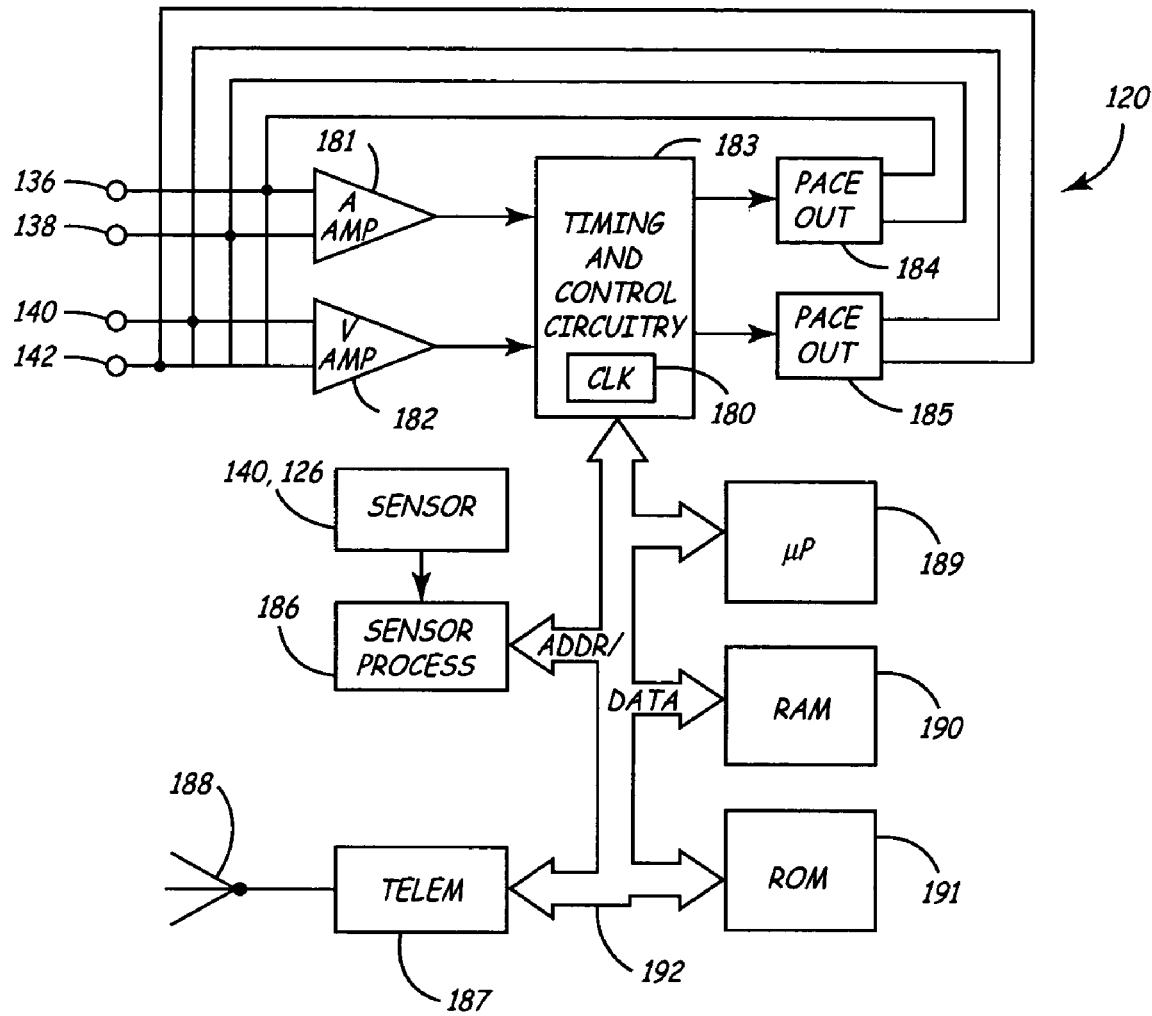
FIG. 4 is a functional schematic diagram of the pacemaker 120 illustrated in FIG. 2.

FIG. 4 is a functional schematic diagram of the pacemaker 120 illustrated in FIG. 2. The pacemaker of FIGS. 2 and 4 is essentially a set of subcomponents of the implantable pacemaker/cardioverter/defibrillator illustrated in FIGS. 1 and 3. Like the device of FIG. 3, the pacemaker is a microprocessor controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 3. Similarly, ventricular electrodes 140 and 142 are coupled to ventricular amplifier 182, which may correspond to ventricular amplifier 200 in FIG. 3. The outputs of atrial and ventricular amplifiers 181 and 182 are input into timing and control circuitry 183 which conforms generally to the pacer timing and control circuitry 212 of FIG. 3, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 3 are produced by atrial and ventricular pulse generator circuits 184 and 185 which may correspond to pulse generator circuits 214 and 216 in FIG. 3. In addition, timing and control circuitry 183 includes a clock 180 used for determining when to perform an escape rate variation session according to the present invention, as described below.

The sensor illustrated in FIG. 4 may correspond to either an activity sensor 126 as described in conjunction with FIG. 2 above or to a hemodynamic sensor 140, as described in conjunction with FIG. 2. If the sensor is an activity sensor, then sensor processing circuitry 186 may correspond to sensor processing circuitry 342 discussed in conjunction with FIG. 3. However, if the sensor is a hemodynamic sensor, the sensor processing circuitry would correspond to the sort of processing circuitry typically associated with hemodynamic sensors. Telemetry circuitry 187 in conjunction with antenna 188 serves to transmit information to and receive information from an external programmer as described above in conjunction with the device of FIG. 3, including information related to stored median interval values and heart rate variability measurements in RAM 190, as calculated by microprocessor 189.

Figure 5:
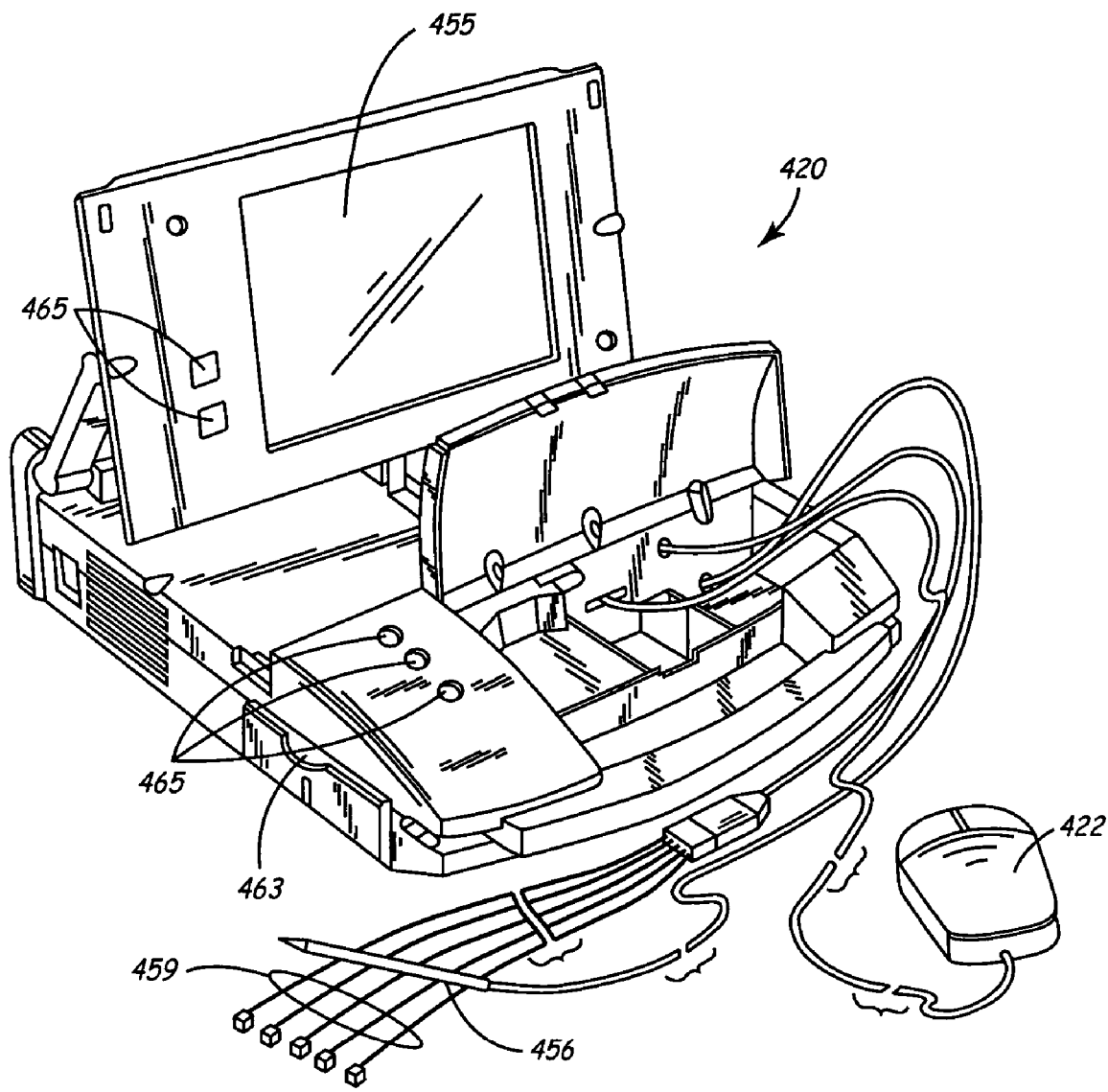
FIG. 5 is a plan view of an external programmer of a sort appropriate for use in conjunction with the practice of the present invention in conjunction with any of the devices of FIGS. 1 and 2.

FIG. 5 is a plan view of an external programmer of a sort appropriate for use in conjunction with the practice of the present invention in conjunction with any of the devices of FIGS. 1 and 2. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylist 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device, including diagnostic information such as sessions that were initiated, the time that they were initiated, and whether they terminated upon normal completion of the session or prior to completion of the session in response to a termination event, as described below.

The programmer is further provided with a printer 463 which allows for hard copy records of displays of signals received from the implanted device such as electrograms, stored parameters, programmed parameters, and information as to heart rate variability and heart rate trends and other diagnostic information. While not visible in this view, the device may also be provided with a floppy disk or CD ROM drive and/or a port for insertion of expansion cards such as P-ROM cartridges, to allow for software upgrades and modifications to the programmer 420.

In the context of the present invention, programmer 420 may serve simply as an input device, a display device, displaying information with regard to heart rate variability as calculated by the implanted device or instead may receive uplinked raw data related to heart intervals and may calculate the heart rate trends and heart rate variability values according to the present invention. It is believed that it is preferable for the implanted device to perform the bulk of the computations necessary to practice the invention, and in particular that it is preferable for the implanted device to at least calculate median rate values, to reduce the storage requirements within the implanted device. However, allocation of functions between the implanted device and the programmer may differ from the preferred embodiments and still result in a workable system.

Figure 6:
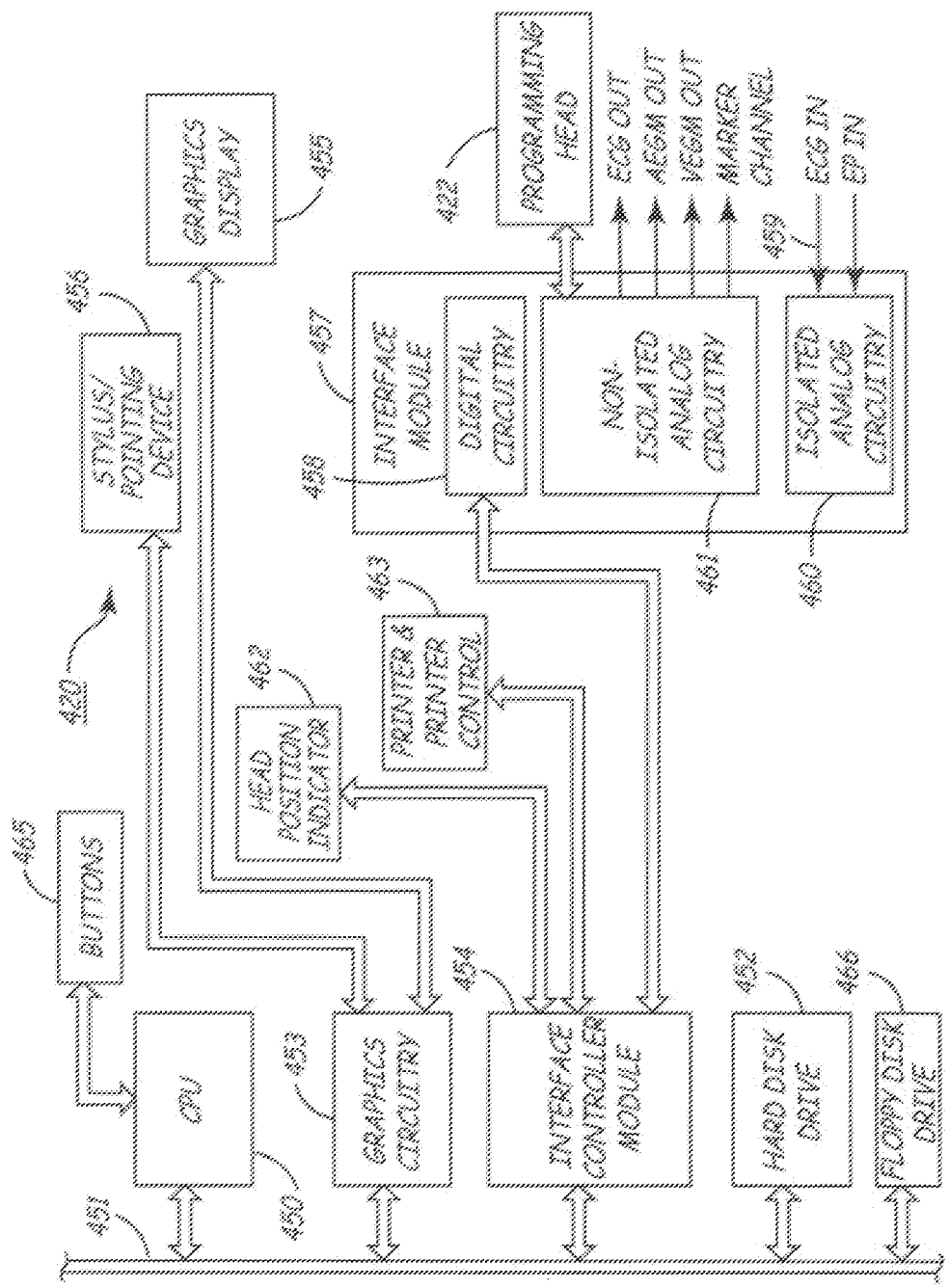
FIG. 6 is a functional schematic of a programmer as illustrated in FIG. 5 appropriate for use in conjunction with the invention.

FIG. 6 is a functional schematic of a programmer as illustrated in FIG. 5 appropriate for use in conjunction with the invention. Programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data and with a graphics circuit 453 and an interface controller module 454. A floppy disk drive 466 or a CD ROM drive is also coupled to bus 451 and is accessible via a disk insertion slot within the housing of the programmer 420. Programmer 420 further includes an interface module 457, which includes digital circuit 458, non-isolated analog circuit 461, and isolated analog circuit 460. Digital circuit 458 enables interface module 457 to communicate with interface controller module 454.

In order for the physician or other caregiver or user to communicate with the programmer 420, control buttons 465 or optionally a keyboard coupled to CPU 450 are provided. However the primary communication mode is through graphics display screen 455 of the well-known "touch sensitive" type controlled by graphics circuit 453. A user of programmer 420 may interact therewith through the use of a stylus 456, also coupled to graphics circuit 453, which is used to point to various locations on screen 455, which display menu choices for selection by the user or an alphanumeric keyboard for entering text or numbers and other symbols.

Graphics display 455 also displays a variety of screens of telemetered out data or real time data including measurements of heart rate variability and heart rate trends according to the present invention. Programmer 420 is also provided with a strip chart printer 463 or the like coupled to interface controller module 454 so that a hard copy of a patient's ECG, EGM, marker channel or of graphics displayed on the display 455 can be generated.

As will be appreciated by those of ordinary skill in the art, it is often desirable to provide a means for programmer 420 to adapt its mode of operation depending upon the type or generation of implanted medical device to be programmed. Accordingly, it may be desirable to have an expansion cartridge containing EPROMs or the like for storing software programs to control programmer 420 to operate in a particular manner corresponding to a given type or generation of implantable medical device. In addition, in accordance with the present invention, it is desirable to provide the capability through the expansion cartridge or through the floppy disk drive 66 or CD ROM drive.

The non-isolated analog circuit 461 of interface module 457 is coupled to a programming head 422 which is used to establish the uplink and downlink telemetry links between the pacemaker 120 and programmer 420 as described above. Uplink telemetered EGM signals are received in programming head 422 and provided to non-isolated analog circuit 461. Non-isolated analog circuit 461, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers be received by programming head 422 are presented on the MARKER CHANNEL output line from non-isolated analog circuit 461.

Isolated analog circuit 460 in interface module 457 is provided to receive external ECG and electrophysiologic (EP) stimulation pulse signals. In particular, analog circuit 460 receives ECG signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Figure 7:
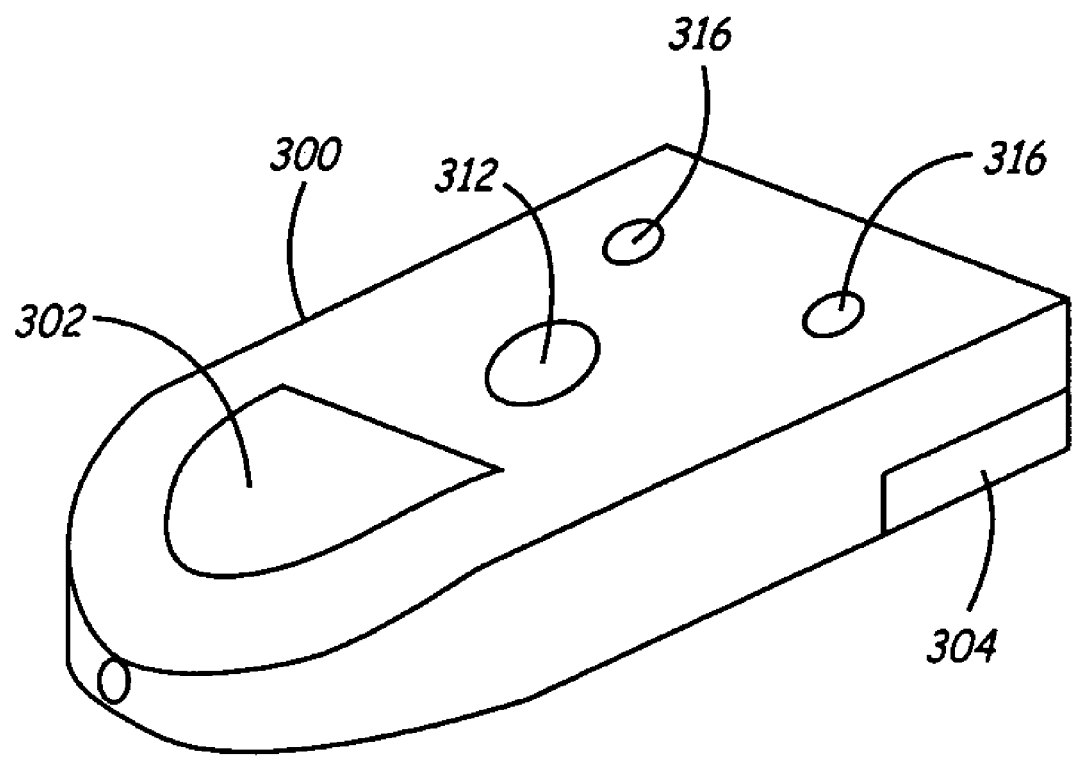
FIG. 7 is a schematic diagram of a patient activator of the type which may be employed with the present invention.

FIG. 7 is a schematic diagram of a patient activator of the type which may be employed with the present invention. The activator 300, which is similar to the patient activator described in U.S. Pat. No. 5,836,975 to DeGroot, incorporated herein by reference in its entirety, generally takes the form of a plastic enclosure provided with a push button 302 by which the patient may request delivery of predefined patient-initiated therapy, including the escape rate variation therapy of the present invention described in detail below. The device is battery powered, employing batteries accessible by means of the battery cover 304. On the reverse side of the device, not visible, are two indicator lights, one green, one amber, which are used to provide information to the patient with regard to the status and functioning of the patient-initiated therapy.

Figure 8:
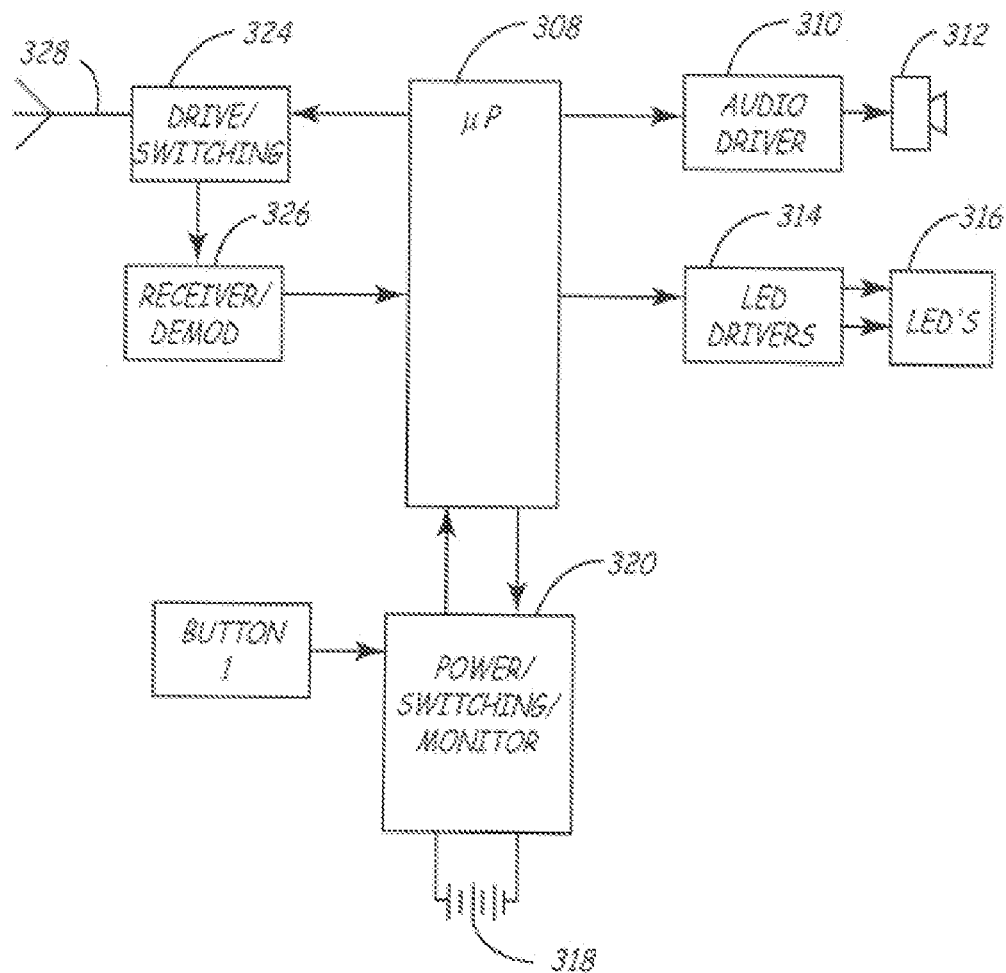
FIG. 8 is a block functional diagram of a patient activator of the type for use in conjunction with the present invention.

FIG. 8 is a block functional diagram of a patient activator of the type for use in conjunction with the present invention. This device corresponds generally to patient activators presently available commercially for use in conjunction with implanted Medtronic pacemakers, and in particular, corresponds generally to the Medtronic Model-9462 patient activator presently in commercial distribution for use in conjunction with implanted bradycardia pacers. Control functions are provided by microprocessor 308, based upon programming stored in its associated read-only memory located therein. Microprocessor 308 provides output signals for producing audible patient alert signals by means of driver 310 and speaker 312. Microprocessor 308 also provides control signals to LED driver 314 to power the associated amber and green colored LEDs 316, referred to above. The device is powered by a battery 318 which is coupled to the microprocessor 308 by means of power/switching/battery monitor circuitry 320, which also provides the microprocessor with an indication that push button 302 has been pressed.

Communication with microprocessor 308 is accomplished by means of the antenna driver/switching circuit 324, the receiver demodulator 326 and RF antenna 328. Transmissions from the implanted device are received by antenna 328, and are demodulated by receiver demodulator 326 to be provided to the microprocessor 189 (FIG. 4) via antenna 188. In response to received transmissions from the implanted device, the microprocessor controls operation of the audio and light drivers 310 and 314 to indicate the nature of the communication received. Transmissions to the implanted device, for example, in response to activation of the push button 302 are provided by microprocessor 308 to the antenna drive/switching circuit, which then communicates with the implanted device by means of antenna 328.

FIG. 9 is a flowchart of a method for varying a parameter in an implantable medical device according to the present invention. Although the method for varying a parameter in an implantable medical device illustrated in FIG. 9 is being described as being utilized in cardiac pacemaker 120, it is understood that the method of varying a parameter of the present invention is not intended to be limited to use in pacemaker 120, and could similarly be employed in other implantable medical devices, such as pacemaker/cardioverter/defibrillator 10, for example.

As illustrated in FIGS. 4 and 9, at some point subsequent to implant of the implantable medical device 120, information regarding the patient, such as coronary artery disease status, heart failure status, date of birth, sex, age, time of day to initiate the escape rate variation method of the present invention, and whether to turn the rate variation feature of the present invention ON or OFF, for example, in addition to other programmable features described below, is input by a physician or clinician, Step 500, via programmer 420. Once the patient information is initiated and the rate variation feature is turned ON, microprocessor 189 determines whether a programmable predetermined time period since the last generation of a histogram was performed has expired, Step 502.

The programmable time period utilized in Step 502 corresponds to the amount of time between generated histograms and should be chosen based on the desired time of day and number of times that the rate variation featured is intended to be initiated. Once the predetermined time period since the last generated histogram has expired, microprocessor 189 generates a histogram of the patient's heart rate, Step 504, described below in reference to FIGS. 10A and 10B, restarts the predetermined time period utilized in Step 502, and determines whether an initiation delay has expired, Step 506. During the initiation delay, application of the parameter variation feature of the present invention is delayed for a predetermined period of time following programming of the device in Step 500 in order for the device to accumulate heart rate data over the predetermined time period and to establish consistency in the accumulated heart rate data over the time period.

Once the rate variation feature initiation delay has expired, microprocessor 189 determines that it is time to initiate a session of the escape rate variation of the present invention in response to a patient activation request being received from patient activator 300 (FIG. 7), or an indication from clock 180 that it is the programmed time of day for initiating the parameter variation of the present invention, Step 508. According to the present invention, the specific number of times and times of the day at which the escape rate variation therapy is to be employed is programmable, and therefore can be set at any desired value, such as two or three times a day, including a morning, afternoon and evening session, for example.

Once it is determined that it is time to initiate a session of the escape rate variation of the present invention, microprocessor 189 compares the most recent generated histogram to a predetermined target rate profile stored in ROM 191, Step 510.

Figure 10A:
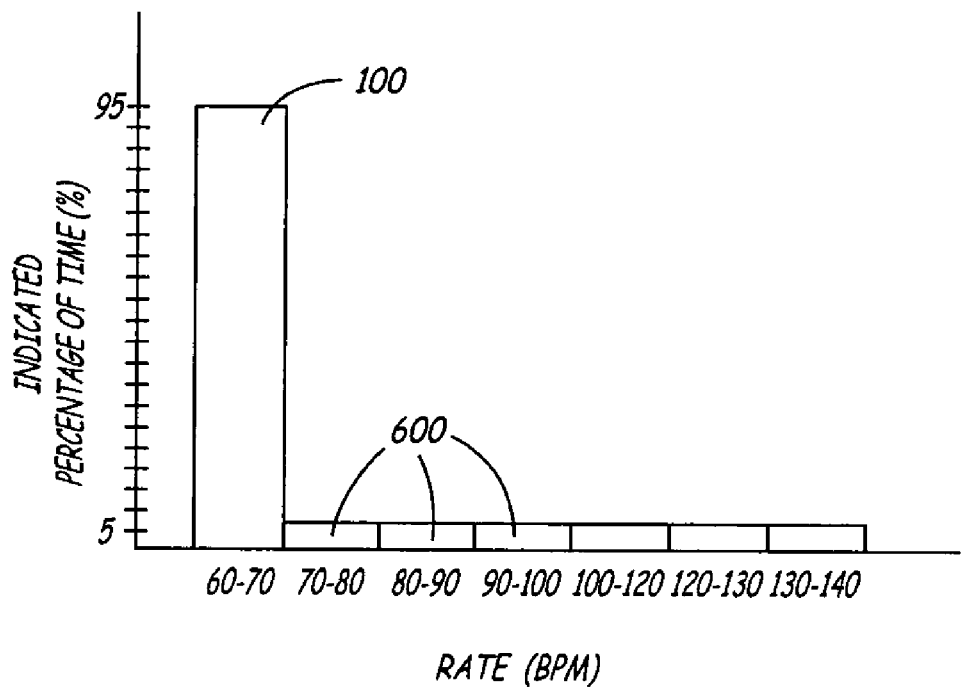
FIG. 10A is a graphical representation of an example of a histogram generated in accordance with the present invention.
Figure 10B:
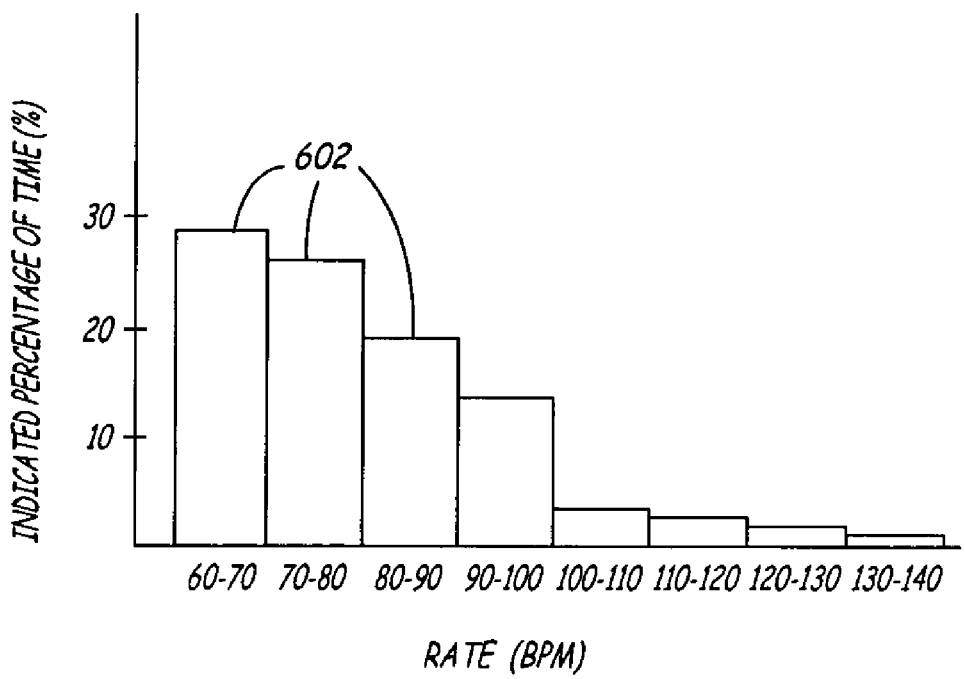
FIG. 10B is a graphical representation of an exemplary target rate profile stored in an implantable medical device according to the present invention.

A histogram presents heart activity data represented by sensed QRS complexes obtained over a period of time in a compact manner, wherein successive intervals between R-waves are computed and classified as a heart rate associated with that interval. FIG. 10A is a graphical representation of an example of a histogram generated in accordance with the present invention. FIG. 10B is a graphical representation of a corresponding exemplary target rate profile stored in an implantable medical device for comparison with the graphical representation of FIG. 10A, according to the present invention. As illustrated in FIGS. 10A and 10B, the x-axis of the graphical display is divided into bins 600, 602 corresponding to a range of beats per minute (BPM) for the R—R intervals, whereas the y-axis provides the percentage of time that the patient's heart rate is within each bin. As each ECG complex is detected over a predetermined time period, the rate in beats per minute is determined, and the percentage of time in the appropriate bin 600 is updated.

It is understood that the present invention is not intended to be limited to generating a histogram based on percentage of time the patient's heart rate is within a given bin, but rather is intended to include displaying the patient's heart rate in terms of quantities other than the percentage of time. For example, a rate profile may be determined using the number of beats occurring in each bin, rather than the percentage of time the heart rate is within each range (bin).

Since patients having an implantable medical device utilizing the escape rate variation of the present invention are typically sedentary, such as patients who are elderly, wheelchair-bound, bed-ridden or likely to spend a majority of the day being paced by the implantable device at the lower or basal rate programmed in the device, the initial generated histogram in such patients will tend to appear as shown in FIG. 10A, with the patient heart rate being very close to the programmed lower pacing rate, i.e., between approximately 60–70 beats per minute, over a large percentage of the time. Such patients typically experience no change or minimal change in their heart rate for an extended period of time. In addition, circadian variations in such patients tend to be far less compared to normal, or non-sedentary patients.

On the other hand, as illustrated in FIG. 10B, the patient heart rate is ideally more evenly distributed over the range of heart rates of the target rate profile, with the percentage of time that the heart rate is within the 60–70 beat per minute range being approximately 30 percent, for example. It is understood that the heart rate percentage values corresponding to the target rate profile stored in ROM 191 are programmable and can be set at any desired distribution in addition to the specific distribution illustrated by example in FIG. 10B. Accordingly, the escape rate variation feature of the present invention is not intended to be limited specifically to the target rate profile as illustrated in FIG. 10B, but rather, includes any desired target rate profile.

Returning to FIGS. 4 and 9, based on the comparison of the generated histogram and the predetermined target rate profile (FIG. 10B) stored in ROM 191, Step 510, microprocessor 189 determines whether a session of the rate variation feature would be appropriate, Step 512. If the session would not be appropriate, the process returns to Step 502, and microprocessor 189 generates an updated histogram after waiting the predetermined time period, and repeats the comparison of the updated histogram with the target rate profile, Steps 502–512. For example, as illustrated in FIGS. 10A and 10B, a session of the rate variation feature of the present invention would be determined to be inappropriate in Step 512 in response to the value of the indicated percent of time that the patient's heart rate within one or more or all of heart rate bins 600 of the generated histogram is approximately equal to corresponding heart rate bins 602 of the target profile rate histogram. On the other hand, a session of the rate variation feature of the present invention would be determined to be appropriate in Step 512 in response to the value of the indicated percent of time that the patient's heart rate within one or more or all of heart rate bins 600 of the generated histogram is less than corresponding heart rate bins 602 of the target profile rate histogram.

According to the present invention, the step of determining whether a session of the rate variation feature would be appropriate, Step 512, may include determining whether there is a constant heart rate or a minimal change in heart rate variations over a period of time, such as four hours, for example. The period of time utilized for determining the constant heart rate or minimal change in heart rate variation is not intended to be limited to four hours, but is programmable and may include any desired period of time that is most appropriate for the specific patient or condition. In this way, the session is initiated when the heart rate is at a constant rate or is less than a predetermined value in order to introduce variability in the heart rate.

Figure 11A:
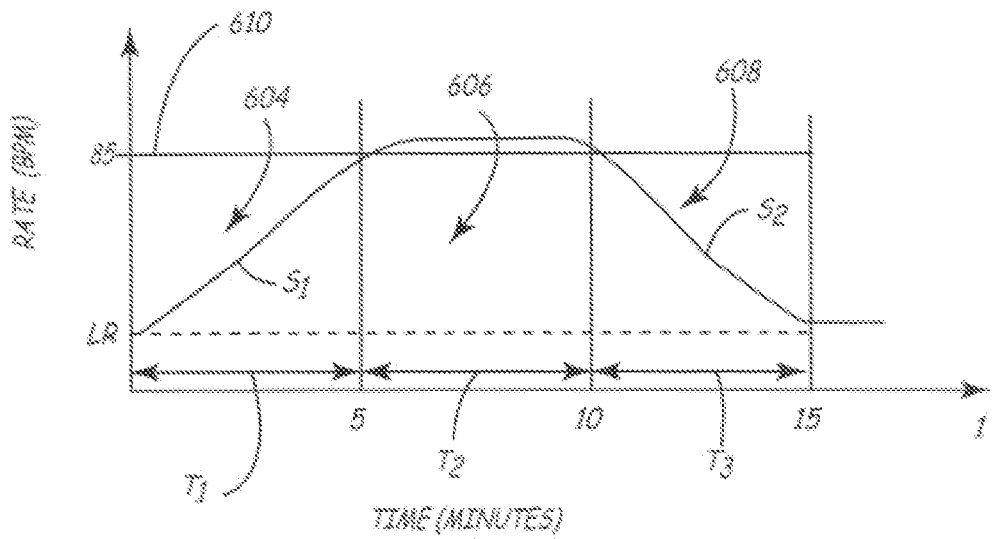
FIGS. 11A–11F are graphical representations of exemplary exercise time profiles according to the present invention.
Figure 11B:
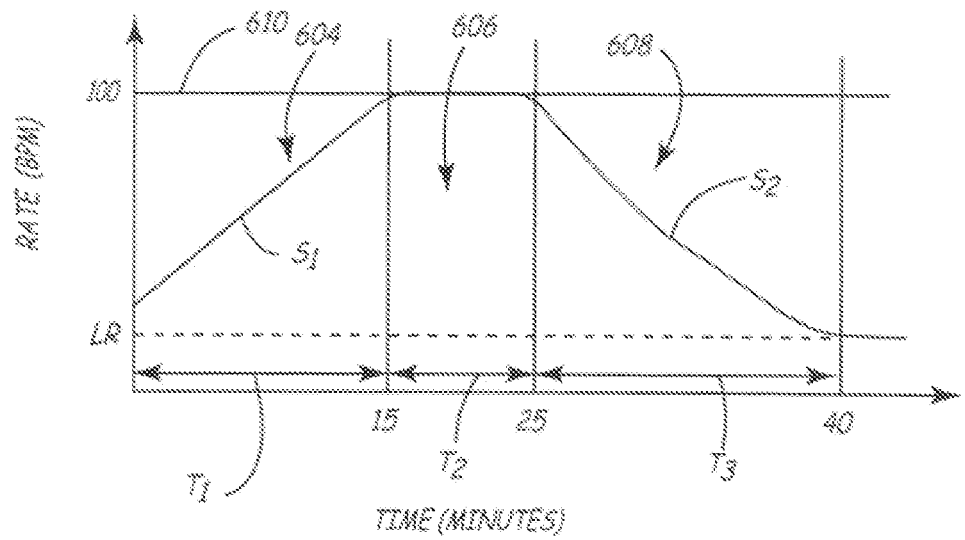

Returning again to FIGS. 4 and 9, once it is determined that a session of the escape rate variation feature of the present invention would be appropriate, microprocessor 189 selects an exercise time profile from exercise time profiles stored in ROM 191, Step 514. FIGS. 11A and 11B are graphical representations of exemplary exercise time profiles according to the present invention. According to the present invention, exercise time profile portion of ROM 191 contains information corresponding to specific time domain rate profiles relating to variations in the pacing rate to simulate numerous exercises, for example, and which are appropriate for specific patients based on factors such as the patient's sex and age. According to an embodiment of the present invention, the exercise rate profile portion includes a number of age appropriate programmable time profiles that vary the pacing rate of the device for a predetermined time period in an attempt to simulate activities of daily living (ADL), such as walking for example, in addition to a number of age appropriate programmable time profiles that vary the pacing rate of the device for a predetermined time period in an attempt to simulate more vigorous exercise. For each available stored exercise rate profile, once the exercise rate profile is selected, microprocessor 189 increases the lower pacing rate of the device from the programmed lower pacing rate to a corresponding exercise simulation rate, indicated by the time profile for that exercise rate profile, for a predetermined period of time to simulate the effects of exercise activity on the patient's heart.

For example, as illustrated in FIG. 11A, in order to simulate an activity of daily living (ADL) time profile, microprocessor 189 increases the programmed lower pacing rate LR to an ADL exercise simulation rate, such as 85 beats per minute, for example, for a predetermined time period, after which the rate is reduced back to the original lower rate LR. In the same way, as illustrated in FIG. 11B, in order to simulate a more vigorous exercise time profile, microprocessor 189 increases the lower pacing rate LR to a more vigorous exercise simulation rate, such as 120 beats per minute, for example, for a predetermined time period, after which the rate is reduced to the original lower rate LR.

As illustrated in FIGS. 11A and 11B, each exercise time profile includes a rate acceleration portion 604, corresponding to a period of time T1 and a shape S1 corresponding to the rate at which the pacing rate is increased from the lower rate LR to an exercise simulation rate 610, a steady-state portion 606, corresponding to a length of time T2 that the exercise simulation rate 610 is maintained, and a rate deceleration portion 608, corresponding to a period of time T3 and a shape S2 corresponding to the rate at which the pacing rate is decreased from the exercise simulation rate 610 to an exercise time profile termination setting, such as a spontaneous rate, a rate response rate, or the lower rate LR. While shape S1 and shape S2 are shown in FIGS. 11A and 11B as being linear, shape S1 and shape S2 could also have a convex, concave, sigmoidal, saw tooth, or stair step shape.

The values of exercise simulation rate 610, rate acceleration portion 604, steady-state portion 606 and rate deceleration portion 608 are patient dependent and are programmed into the device by the clinician or physician, including such factors as the age and sex of the patient, initially, and may include other factors, such as the generated histograms and length of time that the rate variation feature has been performed, as described below. For example, as illustrated in the exemplary time profile illustrated in FIG. 11A, times T1, T2 and T3 are initially 5 minutes, and shapes S1 and S2 are linear as indicated.

Returning again to FIGS. 4 and 9, once the exercise time profile is chosen, microprocessor 189 determines whether the target profile rate would be exceeded if the selected exercise time profile is initiated by the device, Step 516, by determining whether one or more or all bins 600 of the generated histogram would exceed the corresponding one or more or all of bins 602 of the target rate profile. If the target profile rate would be exceeded, microprocessor 189 determines whether all available stored exercise time profiles have been exhausted, Step 518, and if not, selects another exercise time profile, step 514, and repeats the determination of Step 516 for that exercise time profile. On the other hand, if the target profile rate would not be exceeded, microprocessor 189 activates the selected exercise time profile, Step 520. Once the selected exercise time profile is activated, microprocessor 189 continues to monitor the patient to determine whether a termination event that would necessitate terminating the rate variation function of the present invention, such as increased sinus rhythm above the pacing rate, or an atrial or ventricular tachycardia event, for example, is detected during the session, Step 522. If a termination event is detected during the session, the session is terminated, Step 524. According to the present invention, conditions for termination in Step 522 prior to completion of the session include detection of a programming session, magnet, cardiac arrhythmia, or the spontaneous rate or the rate response rate increasing to be greater than the exercise stimulation rate 610.

Once the session is completed, YES in Step 524, or terminated, Step 526, the pacing rate is returned from the exercise simulation rate 610 back to a termination setting, which corresponds to deceleration portion 608 reaching either the spontaneous rate if greater than the lower pacing rate LR, the rate response rate if greater than the lower pacing rate LR, or the original lower pacing rate LR, for example, the process returns to Step 502, and microprocessor 189 generates an updated histogram after waiting the predetermined time period, and repeats the comparison of the updated histogram with the target rate profile, Steps 502–512. The session is determined to be completed in Step 524, for example, once the total of time periods T1, T2 and T3 has expired.

Information corresponding to when a session has been terminated, Step 526, completed Step 524, or when the profiles have been exhausted Step 518, is stored for later retrieval as diagnostic information. In this way, a physician may retrieve diagnostic information related to what exercise sessions were initiated by the device, when each of the initiated sessions started, when the sessions were terminated, and whether the sessions were terminated due to normal conditions, i.e., deceleration portion 608 reaching either the spontaneous rate, the rate response rate, or the original lower pacing rate LR (Step 524), or were due to the detection of a termination event, such as detection of a programming session, magnet, cardiac arrhythmia, or the spontaneous rate or the rate response rate increasing to be greater than the exercise stimulation rate 610 (Steps 522 and 526).

According to an embodiment of the present invention, in determining whether exercise is appropriate based on the comparison of the generated histogram and the target rate profile (Step 512 of FIG. 9), microprocessor 189 compares the indicated percentage of time that the patient's heart rate in the generated histogram of FIG. 10A is within the 70–80 beat per minute and the 80–90 beat per minute bins 600 with the indicated percentage of time for the corresponding 70–80 and 80–90 beat per minute bins 602 of the target rate profile of FIG. 10B. If either of bins 600 are greater than or approximately equal to bins 602, microprocessor 189 determines that exercise would not be appropriate in Step 512, generates an updated histogram after waiting the predetermined time period, and repeats the comparison of the updated histogram with the target rate profile, Steps 502–512. However, if microprocessor 189 determines that bins 600 are less than bins 602, exercise is determined to be appropriate.

According to an alternate embodiment of the present invention, in which the histogram is generated as a comparison of the number of beats, rather than the percentage of time, the y-axis in FIGS. 10A and 10B represents number of beats. In this embodiment, when determining whether exercise is appropriate based on the comparison of the generated histogram and the target rate profile (Step 512 of FIG. 9), microprocessor 189 compares the indicated number of beats in the generated histogram of FIG. 10A within the 70–80 beat per minute and the 80–90 beat per minute bins 600 with the indicated number of beats in the corresponding 70–80 and 80–90 beat per minute bins 602 of the target rate profile of FIG. 10B. If either of bins 600 are greater than or approximately equal to bins 602, microprocessor 189 determines that exercise would not be appropriate in Step 512, generates an updated histogram after waiting the predetermined time period, and repeats the comparison of the updated histogram with the target rate profile, Steps 502–512. However, if microprocessor 189 determines that bins 600 are less than bins 602, exercise is determined to be appropriate.

Figure 12:
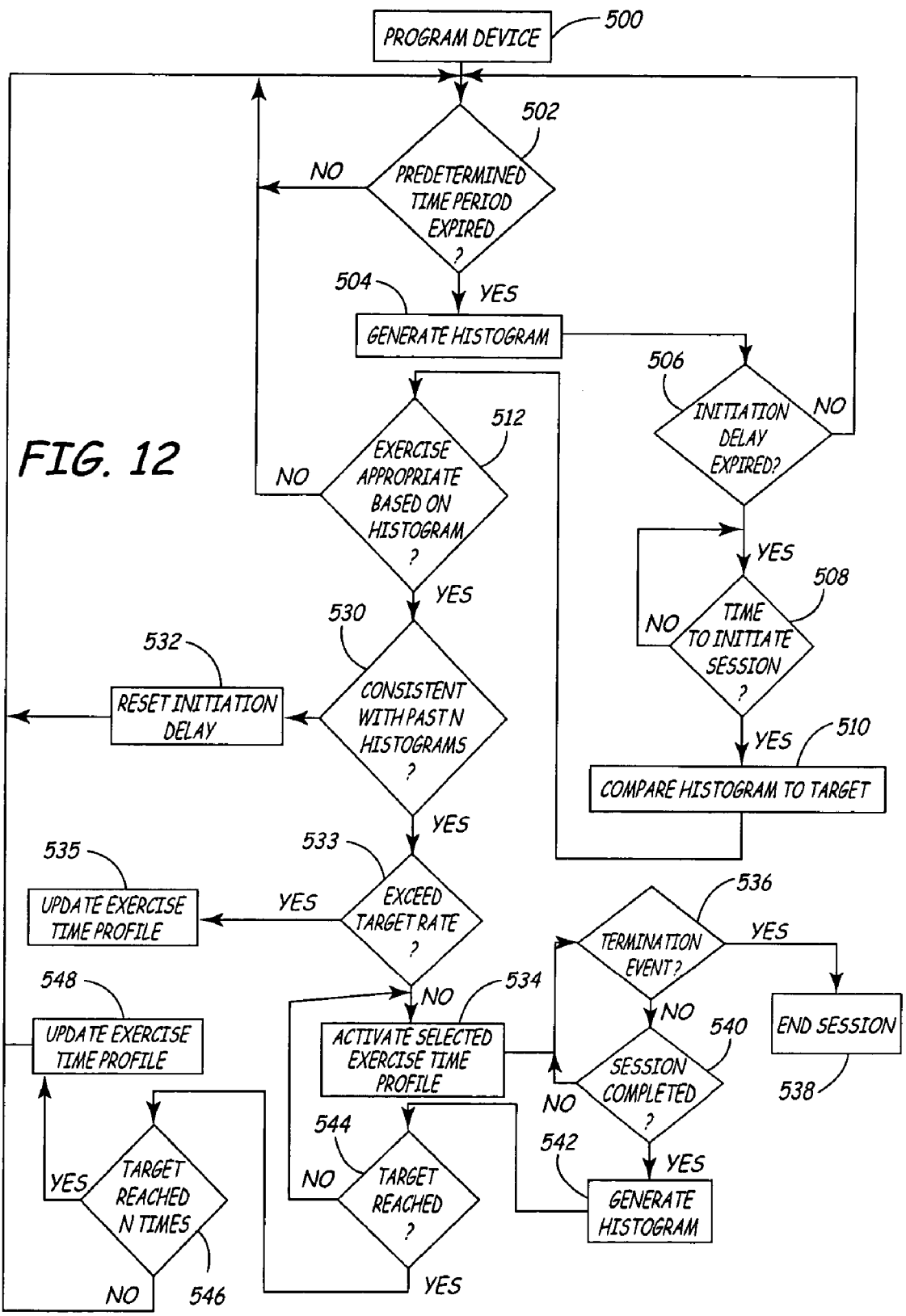
FIG. 12 is a flowchart of a method for varying a pacing rate in an implantable medical device according to the present invention.

FIG. 12 is a flowchart of a method for varying a pacing rate in an implantable medical device according to the present invention. Steps 500–512 in FIG. 12 are similar to Steps 500–512 of FIG. 9 described above, and therefore will not be repeated for the sake of brevity. According to the present invention, the rate variation therapy may be gradually introduced and initiated by the implantable medical device. For example, as illustrated in FIG. 12, according to an embodiment of the present invention, once the session of heart rate variation of the present invention is determined to be appropriate in Step 512, microprocessor 189 determines whether the current generated histogram is consistent with a predetermined number N of previously generated histograms, Step 530. Predetermined number N can be set at any desired value, such as 5 for example, and enables the device to verify that the patient's heart rate consistently remains at approximately the same rate below the target profile rate.

If the current generated histogram is not consistent with the predetermined number N of previously generated histograms, NO in Step 530, microprocessor 189 resets the initiation delay, Step 532, associated with Step 506 so that the implantable device delays application of the escape rate variation feature of the present invention over a predetermined period of time, such as five days as described above, after which Step 530 is repeated. If it is determined that the patient's heart rate consistently remains at approximately the same rate below the target profile rate for the predetermined number N of previously generated histograms, YES in Step 530, a determination is made as to whether a projected histogram including a session of the current selected exercise time profile would result in one or more of bins of the target rate profile to be exceeded, Step 533. If it is projected that one or more bins would be exceeded, the selected exercise time profile is updated by changing one or more of the exercise stimulation rate 610 (which effectively changes the specific bin or bins that are compared with the target rate profile), times T1-T3, and shapes S1 and S2, Step 535. According to an embodiment of the present invention, the process returns to Step 502 immediately upon updating of the exercise time profile in Step 535, and microprocessor 189 generates an updated histogram after waiting the predetermined time period, repeats the comparison of the updated histogram with the target rate profile, Steps 502–512 and performs the subsequent heart rate variation session, Steps 530–548 using the updated exercise time profile. In another embodiment of the present invention, once the exercise time profile is updated in Step 512, a determination is again made as to whether a projected histogram including a session of the current selected exercise time profile would result in one or more of bins of the target rate profile to be exceeded, Step 533. In this embodiment, the number of times that the exercise time profile is updated could be limited to a predetermined number of updates, so that once the predetermined number of updates have been performed without resulting in the corresponding bin or bins of the target rate profile not being exceeded, i.e., without determining NO in Step 533, the process returns to Step 502 and microprocessor 189 generates an updated histogram after waiting the predetermined time period, repeats the comparison of the updated histogram with the target rate profile, Steps 502–512 and performs the subsequent heart rate variation session, Steps 530–548 using either the original exercise time profile or an alternate exercise time profile.

However, according to an alternate embodiment of the invention, if it is projected that one or more bins would be exceeded, YES in Step 533, the process returns to Step 502 without making updates to the exercise time profile, and microprocessor 189 generates an updated histogram after waiting the predetermined time period, repeats the comparison of the updated histogram with the target rate profile, Steps 502–512 and performs the subsequent heart rate variation session, Steps 530–548 using the same exercise time profile. In other words, the updating Step 535 is omitted in the alternate embodiment.

If the projected histogram indicates that one or more bins would not be exceeded, NO in Step 533, microprocessor 189 activates the patient specific ADL exercise time profile, Step 534, so that the implanted device begins pacing at the corresponding exercise simulation rate 610 (FIG. 11A), utilizing the predetermined periods of time T1–T3 and shapes S1 and S2.

Once the selected exercise time profile is activated, microprocessor 189 continues to monitor the patient to determine whether a termination event that would necessitate terminating the rate variability function, such as increased sinus rhythm, or an atrial or ventricular tachycardia event, for example, is detected during the session, Step 536. If a termination event is detected during the session, the session is terminated, Step 538. As described above in reference to FIG. 9, conditions for termination in Step 536 prior to completion of the session include detection of a programming session, magnet, cardiac arrhythmia, or the spontaneous rate or the rate response rate increasing to be greater than the exercise stimulation rate 610.

Once the rate variation session is completed, YES in Step 540, microprocessor 189 generates an updated histogram, Step 542, and determines whether the target rate profile has been reached, Step 544, by comparing the bin 600 corresponding to the exercise simulation rate 610 of the selected exercise time profile, i.e. 85 beats per minute, to the same bin 602 of the target rate profile (FIG. 10B). As described above in reference to FIG. 9, the session is determined to be completed in Step 540, for example, once the total of time periods T1, T2 and T3 has expired.

If the target rate profile is not reached as a result of the activated exercise time profile, NO in Step 544, the exercise time profile is repeated, Step 534, and the determination as to whether the target rate has been reached, Step 544, is repeated based on an updated histogram generated after the repeated session is completed without occurrence of a termination event, Steps 536–542. On the other hand, if the target rate profile is reached as a result of the activated exercise time profile, Yes in Step 544, microprocessor 189 determines whether the target rate profile has been reached a predetermined number N of times, Step 546.

The predetermined number of times N that the target rate profile must be met, which is programmable and could be set at any desired value, enables the pacing rate to be increased to the selected exercise simulation rate 610 the predetermined number N of times prior to adjusting the exercise time profile, Step 548, thereby enabling the heart rate variation feature of the present invention to gradually vary and increase the selected exercise time profile as the patient experiences more and more sessions, similar to normal recommended exercise regimens. In particular, once the target rate profile has been reached a predetermined number N of times, the selected exercise time profile is updated, Step 548, by changing any one or more of the variables in the exercise time profile, such as the exercise simulation rate 610, time periods T1–T3 and shapes S1 and S2.

Once the exercise time profile has been updated, the pacing rate is returned from the exercise simulation rate 610 back to a termination setting, which corresponds to deceleration portion 608 reaching either the spontaneous rate if greater than the lower pacing rate LR, the rate response rate if greater than the lower pacing rate LR, or the lower pacing rate LR, for example, the process returns to Step 502, and microprocessor 189 generates an updated histogram after waiting the predetermined time period, repeats the comparison of the updated histogram with the target rate profile, Steps 502–512 and performs the subsequent heart rate variation session, Steps 530–548 using the updated exercise time profile.

Information corresponding to when sessions have been terminated, Step 538, completed Step 540, when the target rate profile has not been met N times, Step 546, or when the exercise time profiles have been updated or exhausted Steps 535 and 548, is stored for later retrieval as diagnostic information. In this way, a physician may retrieve diagnostic information related to what exercise sessions were initiated by the device, when each of the initiated sessions started, when the sessions were terminated, and whether the sessions were terminated due to normal conditions, i.e., deceleration portion 608 reaching either the spontaneous rate, the rate response rate, or the original lower pacing rate LR, or were due to the detection of a termination event, such as detection of a programming session, magnet, cardiac arrhythmia, or the spontaneous rate or the rate response rate increasing to be greater than the exercise stimulation rate 610.

Figure 11C:
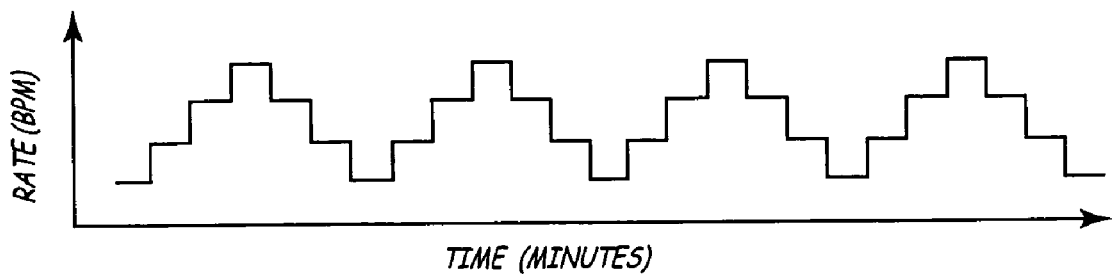
Figure 11D:
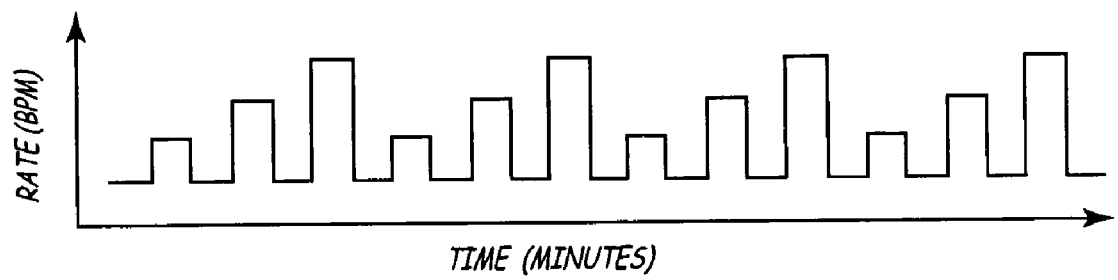
Figure 11E:
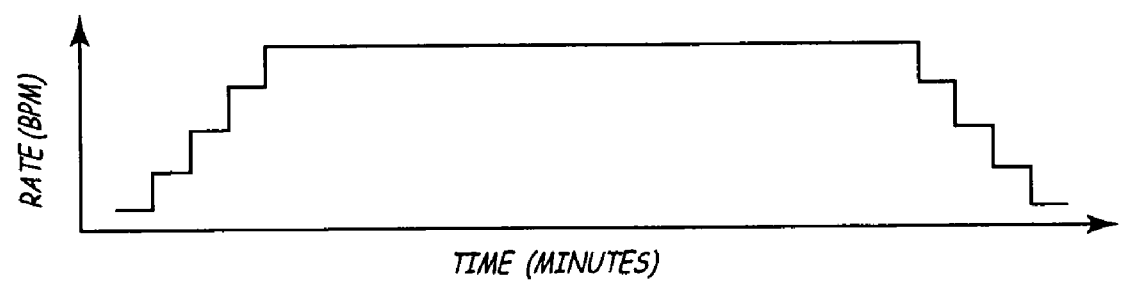
Figure 11F:
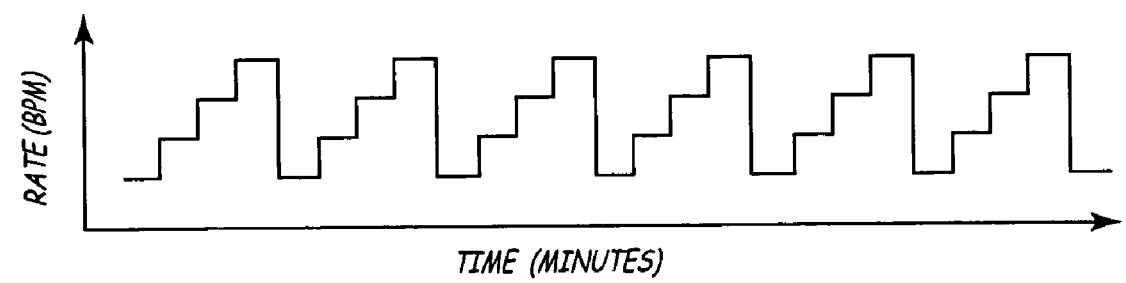

According to an embodiment of the present invention, rather than performing a single iteration of the selected exercise time profile during a given session, the selected exercise time profile, such as shown in FIG. 11A or 11B, for example, could be repeated any number of times, or could include multiple sessions at different exercise simulation rates 610. For example, a single session could include activating the exercise time profile of FIG. 11A three successive times, or could include multiple varied sessions, with one session having one exercise simulation rate, such as 85 beats per minute (FIG. 11A), and a second session having a different exercise simulation rate, such as 100 beats per minute (FIG. 11B), and so forth. In addition to the exercise simulation rate 610, variations in one or more of time periods T1–T3 and shapes S1 and S2 could also be included in the updating procedure. FIGS. 11C–11F present alternate exercise time profiles, with FIG. 11C illustrating stepped heart rate variations to a peak level and then steps back down to the lower rate, for example. FIG. 11D illustrates the same step increase in the paced rate, however, between each step is a period at the lower rate. FIG. 11E illustrates a step rate to a peak rate, which is then maintained for a prolonged period before returning back to the lower rate. FIG. 11F illustrates step increases to the exercise simulation rate, which is then returned to the lower rate. The illustrated variations in the pacing rate, along with those illustrated in FIGS. 11A and 11B, are not meant to be limiting, and illustrate only a few of the numerous possible methods that could be used to vary the heart rate. An appropriate exercise time profile is selected to vary the heart rate to a targeted rate outside the patient's basal variation for a prescribed period according to the selected exercise time profile.

Some of the techniques described above may be embodied as a computer-readable medium comprising instructions for a programmable processor such as microprocessor 189 or pacer timing/control circuitry 183 shown in FIG. 4. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

It is understood that while the above description includes utilizing histogram bins to determine heart rate variability using a time domain, application of the present invention is not intended to be limited to the use of histograms and to the use of a time domain. Rather, the present invention is intended to include other methods for determining heart rate variability, such as standard deviation for example, and domains other than the time domain, such as a frequency domain for example.

While a particular embodiment of the present invention has been shown and described, modifications may be made. It is therefore intended in the appended claims to cover all such changes and modifications, which fall within the true spirit and scope of the invention.

The invention claimed is:

1. A method for temporarily varying a parameter in an implantable medical device, comprising:
   determining heart rate variability;
   comparing the determined heart rate variability to a predetermined target rate profile;
   adjusting the parameter from a first setting to a second setting different from the first setting in response to the comparing of the determined heart rate variability and the predetermined target rate profile; and
   adjusting the parameter from the second setting to a termination setting in response to expiration of a first predetermined time period.

2. The method of claim 1, further comprising determining whether to initiate a varying of a parameter in response to one of receipt of a patient activation and an internal indication of a predetermined time of day for initiating the varying of a parameter.

3. The method of claim 1, further comprising determining whether a varying of a parameter is appropriate in response to the comparing the determined heart rate variability to a predetermined target rate profile.

4. The method of claim 1, wherein determining heart rate variability includes generating a histogram of heart rates having a plurality of corresponding heart rate bins.

5. The method of claim 4, further comprising determining whether a varying of a parameter is appropriate in response to the comparing the determined heart rate variability to a predetermined target rate profile, wherein the varying of a parameter is determined to be appropriate in response to a percentage of time that heart rates are within one or more of the plurality of heart rate bins.

6. The method of claim 4, further comprising determining whether a varying of a parameter is appropriate in response to the comparing the determined heart rate variability to a predetermined target rate profile, wherein the varying of a parameter is determined to be appropriate in response to a number of beats within one or more of the plurality of heart rate bins.

7. The method of claim 1, further comprising determining whether a varying of a parameter is appropriate in response to the comparing the determined heart rate variability to a predetermined target rate profile, wherein the varying of a parameter is determined to be appropriate in response to change in heart rate variability being less than a predetermined value.

8. The method of claim 1, further comprising:
   storing exercise time profiles corresponding to variations in the second setting; and
   selecting a first exercise time profile from the stored exercise time profiles in response to the comparing the determined heart rate variability to a predetermined target rate profile.

9. The method of claim 8, wherein each of the stored exercise time profiles include an acceleration portion corresponding to adjusting the parameter from the first setting to the second setting, a steady-state portion corresponding to the first predetermined time period, and a deceleration portion corresponding to adjusting the parameter from the second setting to the termination setting.

10. The method of claim 9, wherein the first setting corresponds to a predetermined lower pacing rate and the second setting is greater than the predetermined lower pacing rate.

11. The method of claim 8, further comprising:
   determining whether the predetermined target rate profile would be exceeded in response to the first exercise time profile; and
   selecting a second exercise time profile from the stored exercise time profiles in response to the predetermined target profile being exceeded.

12. The method of claim 1, further comprising determining whether to adjust the parameter from the second setting to the termination setting prior to expiration of the first predetermined time period.

13. The method of claim 12, wherein the parameter is adjusted from the second setting to the termination setting prior to expiration of the first predetermined time period in response to one of a programming session, a magnet, a cardiac arrhythmia, spontaneous rate greater than the second setting, and rate response greater than the second setting.

14. The method of claim 1, wherein determining heart rate variability includes generating a histogram of heart rates having a plurality of corresponding heart rate bins, and further comprising, determining, prior to adjusting the parameter from the first setting to the second setting, whether a current generated histogram is consistent with a predetermined number of previously generated histograms.

15. The method of claim 9, further comprising:
determining whether the target rate profile has been reached;
repeating adjusting of the parameter from the first setting to the second setting and from the second setting to the termination setting in response to the target rate profile not being reached; and
updating one or more of the acceleration portion, the steady state portion and the deceleration portion in response to the target rate profile being reached.

16. The method of claim 1, wherein the termination setting corresponds to one of a spontaneous rate, a rate response rate, and the first setting.

17. The method of claim 8, further comprising:
storing information corresponding to the selected exercise time profile; and
outputting the stored information to an external device.

18. An implantable medical device, comprising:
a plurality of electrodes stimulating heart tissue and sensing cardiac signals;
a timing and control device controlling the stimulation of heart tissue by the plurality of electrodes and measuring intervals between the sensed cardiac signals;
a storage device storing the measured intervals; and
a microprocessor determining heart rate variability in response to the stored intervals, comparing the determined heart rate variability to a predetermined target rate profile, adjusting a parameter from a first setting to a second setting different from the first setting in response to the comparing of the determined heart rate variability and the predetermined target rate profile, and adjusting the parameter from the second setting to a termination setting in response to expiration of a first predetermined time period.

19. The device of claim 18, further comprising a patient activator generating a patient request for adjusting the parameter, wherein the timing and control device generates an indication of a programmed time of day for initiating the adjusting of the parameter, and the microprocessor initiates the adjusting of the parameter in response to receipt of one of the patient request from the patient activator and the indication of the programmed time of day from the timing and control unit.

20. The device of claim 18, wherein the microprocessor compares the determined heart rate variability to the predetermined target rate profile and determines the adjusting of the parameter is appropriate in response to the comparing of the determined heart rate variability to the predetermined target rate profile.

21. The device of claim 20, wherein the microprocessor generates a histogram of heart rates having a plurality of corresponding heart rate bins, and determines the adjusting of the parameter is appropriate in response to a percentage of time that heart rates are within one or more of the plurality of heart rate bins.

22. The device of claim 20, wherein the microprocessor generates a histogram of heart rates having a plurality of corresponding heart rate bins, and determines the adjusting of the parameter is appropriate in response to a number of beats within one or more of the plurality of heart rate bins.

23. The device of claim 18, wherein the microprocessor compares the determined heart rate variability to the predetermined target rate profile and determines the adjusting of the parameter is appropriate in response to change in heart rate variability being less than a predetermined value.

24. The device of claim 18, wherein the storage device stores exercise time profiles corresponding to variations in the second setting, and the microprocessor selects a first exercise time profile from the stored exercise time profiles in response to the comparison of the determined heart rate variability to the predetermined target rate profile.

25. The device of claim 24, wherein each of the stored exercise time profiles include an acceleration portion corresponding to adjusting the parameter from the first setting to the second setting, a steady-state portion corresponding to the second setting, and a deceleration portion corresponding to adjusting the parameter from the second setting to the termination setting.

26. The device of claim 25, wherein the first setting corresponds to a predetermined lower pacing rate and the second setting is greater than the predetermined lower pacing rate.

27. The device of claim 24, wherein the microprocessor determines whether the predetermined target rate profile would be exceeded in response to the first exercise time profile, and selects a second exercise time profile from the stored exercise time profiles in response to the predetermined target profile being exceeded.

28. The device of claim 18, wherein the microprocessor adjusts the parameter from the second setting to the termination setting, prior to expiration of the first predetermined time period, in response to detecting one of a programming session, a magnet, a cardiac arrhythmia, spontaneous rate greater than the second setting, and rate response greater than the second setting.

29. The device of claim 18, wherein the microprocessor generates a histogram of heart rates and determines, prior to adjusting the parameter from the first setting to the second setting, whether a current generated histogram is consistent with a predetermined number of previously generated histograms.

30. The device of claim 25, wherein the microprocessor determines whether the target rate profile has been reached, repeats adjusting of the parameter from the first setting to the second setting and from the second setting to the termination setting in response to the target rate profile not being reached, and updates one or more of the acceleration portion, the steady state portion, and the deceleration portion in response to the target rate profile being reached.

31. The device of claim 18, wherein the termination setting corresponds to one of a spontaneous rate, a rate response rate, and the first setting.

32. The device of claim 24, further comprising an output device outputting information corresponding to the selected exercise time profiles.

33. An implantable medical device, comprising:
means for determining heart rate variability;
means for comparing the determined heart rate variability to a predetermined target rate profile;
means for adjusting a parameter from a first setting to a second setting different from the first setting in response to the comparing of the determined heart rate variability and the predetermined target rate profile; and
means for adjusting the parameter from the second setting to a termination setting in response to expiration of a first predetermined time period.

34. A computer readable medium having computer executable instructions for performing a method comprising:
determining heart rate variability;
comparing the determined heart rate variability to a predetermined target rate profile;
adjusting the parameter from a first setting to a second setting different from the first setting in response to the comparing of the determined heart rate variability and the predetermined target rate profile; and
adjusting the parameter from the second setting to a termination setting in response to expiration of a first predetermined time period.

35. An implantable medical device, comprising:
means for stimulating heart tissue and sensing cardiac signals;
means for controlling timing of the stimulation of heart tissue and measuring intervals between the sensed cardiac signals;
means for determining heart rate variability in response to the intervals;
means for comparing the determined heart rate variability to a predetermined target rate profile;
means for adjusting a parameter from a first setting to a second setting different from the first setting in response to the comparing of the determined heart rate variability and the predetermined target rate profile, and adjusting the parameter from the second setting to a termination setting in response to expiration of a first predetermined time period;
means for selecting a first exercise time profile from stored exercise time profiles in response to the comparison of the determined heart rate variability to the predetermined target rate profile, each of the stored exercise time profiles including an acceleration portion corresponding to adjusting the parameter from the first setting to the second setting, a steady-state portion corresponding to the first predetermined time period, and a deceleration portion corresponding to adjusting the parameter from the second setting to the termination setting, wherein the adjusting means adjusts the parameter from the second setting to the termination setting, prior to expiration of the first predetermined time period, in response to detecting one of a programming session, a magnet, a cardiac arrhythmia, spontaneous rate greater than the second setting, and rate response greater than the second setting.

36. The device of claim 35, further comprising means for generating a patient request for adjusting the parameter, wherein the controlling means generates an indication of a programmed time of day for initiating the adjusting of the parameter, and the adjusting means initiates adjusting of the parameter in response to one of the patient request and the indication of the programmed time of day for initiating the adjusting of the parameter.

37. The device of claim 36, wherein the determining means generates a histogram of heart rates having a plurality of corresponding heart rate bins, and determines the adjusting of the parameter is appropriate in response to a percentage of time that heart rates are within one or more of the plurality of heart rate bins.

38. The device of claim 35, wherein the determining means generates a histogram of heart rates having a plurality of corresponding heart rate bins, and determines the adjusting of the parameter is appropriate in response to a number of beats within one or more of the plurality of heart rate bins.

39. The device of claim 35, wherein the first setting corresponds to a predetermined lower pacing rate and the second setting is greater than the predetermined lower pacing rate.

40. The device of claim 35, wherein the comparing means determines whether the predetermined target rate profile would be exceeded in response to the first exercise time profile, and selects a second exercise time profile from the stored exercise time profiles in response to the predetermined target profile being exceeded.

41. The device of claim 35, wherein the determining means generates a histogram of heart rates and determines, prior to the adjusting of the parameter from the first setting to the second setting, whether a current generated histogram is consistent with a predetermined number of previously generated histograms.

42. The device of claim 35, wherein the comparing means determines whether the target rate profile has been reached, and the adjusting means repeats adjusting of the parameter from the first setting to the second setting and from the second setting to the termination setting in response to the target rate profile not being reached, and updates one or more of the acceleration portion, the steady state portion and the deceleration portion in response to the target rate profile being reached.

43. The device of claim 35, wherein the termination setting corresponds to one of a spontaneous rate, a rate response rate, and the first setting.

44. The device of claim 37, further comprising means for outputting information corresponding to the selected exercise time profiles.

* * * * *